United States Patent [19]

Scott et al.

[11] Patent Number: 4,882,272
[45] Date of Patent: Nov. 21, 1989

[54] HIGH MOLECULAR WEIGHT KININOGEN ASSAY

[75] Inventors: Cheryl F. Scott, Bensalem; Robert W. Colman, Moylan, both of Pa.

[73] Assignee: Temple University - of the Commonwealth System of Higher Education, Philadelphia, Pa.

[21] Appl. No.: 11,963

[22] Filed: Feb. 6, 1987

Related U.S. Application Data

[63] Continuation-in-part of Ser. No. 914,029, Oct. 1, 1989, abandoned.

[51] Int. Cl.$^4$ ............................................. C12Q 1/56
[52] U.S. Cl. ....................................... 435/13; 435/23; 435/24
[58] Field of Search ............... 435/13, 23, 24, 183, 435/184, 213, 214, 217, 219

[56] References Cited

U.S. PATENT DOCUMENTS 4,598,043  7/1986  Svendsen ........................... 435/13

OTHER PUBLICATIONS

Scott et al., "Amidolytic Assay of Human Factor XI in Plasma: Comparison with a Coagulant Assay and a New Rapid Radioimmunoassay", *Blood* 63:42-50 (1984).

*Primary Examiner*—Robert Benson
*Attorney, Agent, or Firm*—Seidel, Gonda, Lavorgna & Monaco

[57] ABSTRACT

An assay for functional high molecular weight kininogen in plasma is provided. A plasma sample of unknown functional high molecular kininogen content is treated to inactivate plasma protease inhibitors and kallikrein, and is appropriately neutralized and diluted. Exogenous factor XIIa and factor XI are added to the sample to form a reaction mixture which is incubated with a contact-activating surface. The concentrations of factor XIIa and factor XI in the reaction mixture are selected such that the concentration of functional high molecular weight kininogen in the sample is rate-limiting in the HMWK-mediated activation of factor XI by factor XIIa. The amount of factor XIa generated in the sample, which under the conditions of the assay is directly proportional to the concentration of functional HMWK, may be determined by functional assay using an appropriate factor XIa substrate.

21 Claims, 1 Drawing Sheet

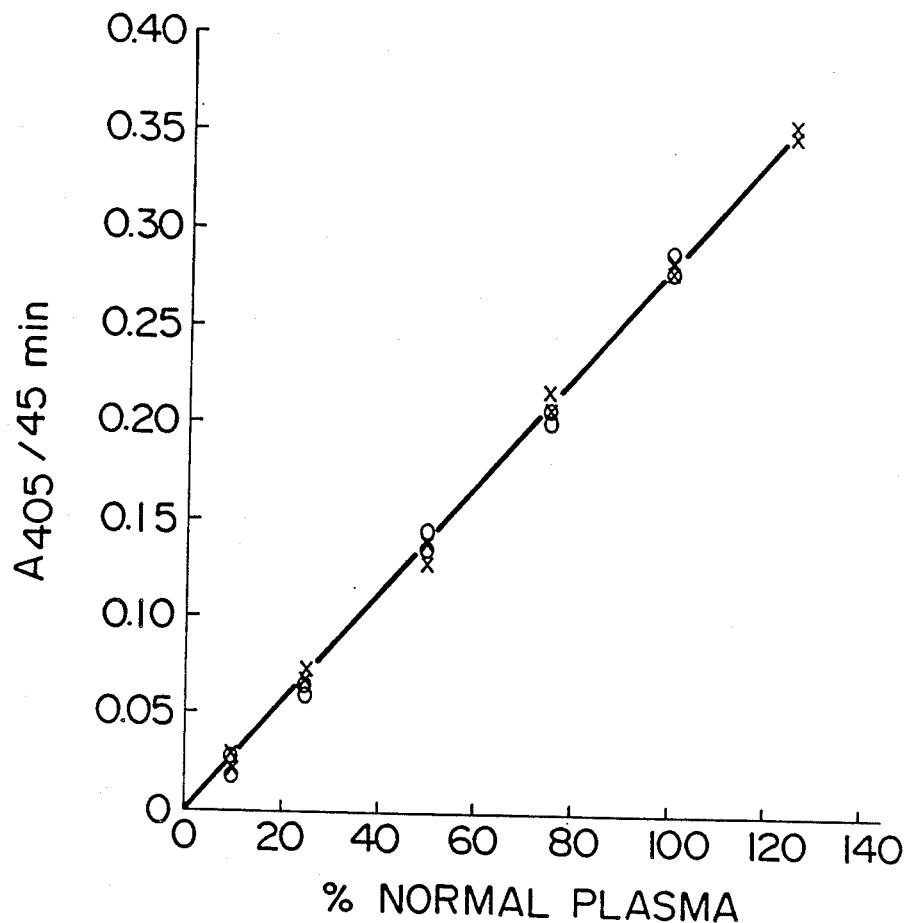

HIGH MOLECULAR WEIGHT KININOGEN ASSAY

REFERENCE TO GOVERNMENT GRANT

The invention described herein was supported by National Institutes of Health Grant HL24365. The United States government has certain rights in the invention.

This is a continuation-in-part of our co-pending application Ser. No. 914,029, filed Oct. 1, 1986, abandoned.

FIELD OF THE INVENTION

The invention relates to a simple and rapid method for determining the amount of functional high molecular weight kininogen in human plasma.

BACKGROUND OF THE INVENTION

High molecular weight kininogen (HMWK) is one of four plasma proteins which are involved in the contact system of plasma proteolysis and are modulatory proteins for coagulation, fibronolysis, complement activation, prorenin activation, and possibly other biochemical pathways occurring in the plasma. The other contact proteins are prekallikrein (also known as Fletcher factor), factor XII (also known as Hageman factor) and factor XI (also known as plasma thromboplastin antecedent).

The plasma kininogens are single-chain glycoproteins which are present in human blood plasma and tissues in two forms: high molecular weight kininogen (120 kDa) and low molecular weight kininogen (64 kDa). Both kininogens are parent molecules for the nonapeptide bradykinin, the most potent naturally-occurring vasodilatory substance. High molecular weight kininogen also functions as a cofactor for the activation of the following plasma zymogens: prekallikrein, factor XI, and indirectly, factor XII.

Factor XI in plasma is activated in vitro by surface-bound activated factor XII (factor XIIa). Factor XIIa arises from the interaction of factor XII zymogen with negatively-charged surfaces. The process is amplified by kallikrein-mediated proteolysis of factor XII, and is further amplified when kallikrein is surface-bound via high molecular weight kininogen.

High molecular weight kininogen forms a complex with factor XI and is responsible for transporting the factor XI zymogen to a negatively-charged surface, upon which it is converted to the active enzyme factor XIa by factor XIIa.

The surface-mediated activation of the proteins of the contact phase of plasma proteolysis occurs in certain pathological conditions such as gram negative sepsis, typhoid fever, and acute attacks of hereditary angioedema. Contact activation may also occur during exposure of plasma to foreign surfaces, such as during hemodialysis, extracorporeal circulation, and implantation of artificial organs and grafts.

Present methods for measuring high molecular weight kininogen include (1) functional coagulant assays, (2) immunologic assays for HMWK, and (3) bioassays and immunoassays for the peptide bradykinin. Each method has limitations and/or drawbacks.

The coagulant assay relies on plasma from an individual with a congenital deficiency of high molecular weight kininogen. Less than ten individuals with this defect have been described in the literature, to date:

Fitzgerald - Saito et al, *J. Clin. Invest.* 55: 1082–1089
Williams - Colman et al, *J. Clin. Invest.* 56: 1650–1662
Flaujeac - Wuepper et al, *J. Clin. Invest.* 56: 1663–1672
Washington - Donaldson et al, *J. Lab Clin. Med.* 87: 327–337
Reid - Lutcher, *Clin. Res.* 24: 440A (1976) (abstract)
Fujiwara - Oh-Ishi et al, *Adv. Exp. Med. Biol.* 120B: 93–99

Coagulation assays, in general, have a high coefficient of variation, and the HMWK coagulant assay relies on rare, congenitally-deficient plasma as substrate.

Immunological determinations for measuring high molecular weight kininogen include rocket electrophoresis: Bouma et al, *J. Lab. Clin. Med.* 96: 693–709 (1980); radioimmunoassay: Proud et al, *J. Lab. Clin Med.* 95: 563–574 (1980); Syvanen et al, *Febs. Letters* 129: 241–245 (1981); Uchida et al, *Throm. Res.* 15: 127–134 (1979); Kerbiriou-Nabias et al, *Brit. J. Haematol.* 56: 273–286 (1984); and hemagglutination inhibition: Kleniewski et al, *Proc. Soc. Exp. Biol. Med.* 156: 113–117 (1977). Such immunological assays for high molecular weight kininogen are time-consuming. They measure the amount of HMWK protein only, without regard to its activity. These methods yield no information concerning the functional integrity of the protein.

While the above-cited hemagglutination inhibition reaction requires less time than other immunoassays, it is laborious and requires many controls. In addition, care must be taken when preparing an antibody to HMWK to assure that it does not cross-react with low molecular weight kininogen, which has the same heavy chain as HMWK.

Bioassays for bradykinin require the sacrificing of an animal and are technically difficult to perform. Radioimmunoassays for bradykinin require special antisera. Damkjaer et al, *Clin. Chem. Acta* 125: 145–156 (1982); van Rosevelt et al, *Clin. Chem. Acta* 126: 81–89 (1982); van Leeuwen et al, *Clin. Chem. Acta.* 127: 343–351 (1983). Most importantly, the available assays for bradykinin cannot distinguish between the high and low molecular weight forms of kininogen. They thus tell nothing of the contact-cofactor function of high molecular weight kininogen.

What is needed is an inexpensive, rapid and reliable assay for determining the level of functional high molecular weight kininogen in human plasma which can be performed in a clinical setting. An assay employing a synthetic substrate has the advantages of being stable as well as reproducible from one laboratory to another. Synthetic chromogenic substrates have been developed to assay a wide variety of enzymes and cofactors. However, since most chromogenic substrates are hydrolyzed by a wide range of proteases, any assay procedure relying on such substrates must be specific for the protein in question.

While a specific chromogenic assay for factor XI in plasma has been reported utilizing a synthetic chromogenic factor XIa substrate, Scott et al, *Blood* 63: 42–50 (1984), the assay provides no information concerning the level of functional HMWK. Although this assay will give a negative result in the total absence of HMWK, a negative result is not necessarily indicative of the absence of functional HMWK, since the assay will also fail in the absence of factor XII.

Hereinafter, "HMWK" shall mean high molecular weight human kininogen.

SUMMARY OF THE INVENTION

An assay for functional HMWK is provided which does not require rare HMWK-deficient plasma. The assay is reproducible, and relatively easy and inexpensive to perform. Numerous samples may be assayed in less than two hours. The assay relies on available natural, or preferably synthetic, substrates for factor XIa. Where chromogenic substrates are employed, the assay may be conducted using a spectrophotometer or suitable microplate-reader device.

According to the present invention, plasma protease inhibitors are substantially completely inactivated in an appropriate plasma specimen. The specimen is diluted with buffer. Prekallikrein activation and kallikrein activity in the diluted specimen are substantially completely inhibited by the addition of, for example, soybean trypsin inhibitor. A reaction mixture comprising the diluted specimen, a contact-activating surface, and selected amounts of factor XIIa and factor XI is formed to initiate HMWK-dependent activation of factor XI. The amounts of factor XIIa and factor XI are selected such that at a selected temperature and selected reaction time, the concentration of functional HMWK is rate-limiting and directly proportional to the concentration of factor XIa generated in the reaction mixture during the HMWK-dependent activation of factor XI; the word "selected" means the same thing as predetermined. The factor XIIa in the reaction mixture is then substantially completely inactivated at the selected reaction time. The amount of factor XIa thus formed in the reaction mixture is functionally assayed, said amount of factor XIa being directly proportional to the amount of functional HMWK in the specimen. The functional assay preferably utilizes a synthetic chromogenic or fluorogenic substrate for factor XIa.

In a preferred embodiment of the invention, plasma protease inhibitors (Cl-inhibitor, alpha$_2$-macroglobulin, alpha$_1$-antitrypsin and antithrombin III) are substantially completely inactivated in a plasma specimen by acid denaturation and dilution. Soybean trypsin inhibitor, factor XIIa, factor XI and a contact-activating surface are added to the specimen to form a reaction mixture. The amount of soybean trypsin inhibitor added to the specimen is sufficient to establish a molar excess of soybean trypsin inhibitor to prekallikrein in the reaction mixture. The amount of factor XIIa added to the specimen is sufficient to establish a molar excess of factor XIIa to HMWK in the reaction mixture. The reaction mixture is incubated for a time sufficient to activate not more than about 10%, preferably not more than about 5%, of the factor XI in the reaction mixture. Further activation of factor XI is prevented by adding sufficient corn trypsin inhibitor, or other suitable inhibitor of factor XIIa, to the reaction mixture to establish a molar excess, preferably at least a 50-fold molar excess, of corn trypsin inhibitor to factor XIIa. The amount of factor XIa formed in the reaction mixture is assayed by hydrolysis of a substrate for factor XIa.

DESCRIPTION OF THE FIGURE

The FIGURE is a standard curve for functional HMWK versus absorbance at 405 nm generated from plasma from a pool of 20 normal donors using buffer (x) or HMWK-deficient plasma (o) as the diluents.

DETAILED DESCRIPTION OF THE INVENTION

HMWK is an essential co-factor for the surface activation of plasma factor XI to factor XIa by plasma factor XIIa. Upon incubation of plasma with a negatively-charged surface (e.g, kaolin), the zymogen factor XII is converted to its enzymatic form, factor XIIa. Factor XIIa in turn activates factor XI much more efficiently when factor XI is bound to a negatively-charged surface than when it is in the fluid-phase. Factor XI will not reach the surface, however, unless it is transported there in a binary, noncovalent complex by its co-factor, HMWK. Therefore, in diluted plasma with factor XIIa and factor XI supplied in excess of HMWK as purified reagents, the concentration of HMWK becomes rate-limiting in the activation of factor XI to factor XIa. The amount of factor XIa thus formed may be conveniently determined through hydrolysis of an appropriate substrate for factor XIa. Chromogenic and fluorogenic substrates are preferred. Under the conditions of the assay, the amount of factor XIa formed is directly proportional to the amount of functional HMWK in the specimen.

Although the factor XIa substrates utilized are not necessarily specific for factor XIa, the conditions of the assay system allow only the activation and expression of factor XIa enzymatic activity. All other enzymes in the assay reaction mixture capable of hydrolyzing the substrate, e.g., kallikrein and factor XIIa, are substantially completely inactivated before introduction of the factor XIa substrate. Inactivation of plasma protease inhibitors before conducting the assay assures that factor XIa, once formed, and exogeneous factor XIIa, remain functional during the course of the factor XI activation step.

The principal protease inhibitors present in normal human plasma are Cl inhibitor, alpha$_2$-macroglobulin, alpha$_1$-antitrypsin (also known as alpha$_1$-protease inhibitor) and antithrombin III. Cl inhibitor and alpha$_2$-macroglobulin are the major inhibitors of kallikrein. While alpha$_1$-antitrypsin is the major inhibitor of factor XIa, Cl inhibitor accounts for greater than 95% of factor XIIa inhibition. The effect of each of these inhibitors in the plasma specimen should be substantially completely neutralized under the conditions of the assay before proceeding with the activation step.

While it is known that treatment of plasma with chloroform inactivates Cl inhibitor, the inactivation is readily reversible. Moreover, alpha$_2$-macroglobulin is not inactivated by chloroform.

The plasma protease inhibitors may be inactivated by a mixture of chloroform and methylamine, since methylamine inactivates alpha$_2$-macroglobulin. This treatment, while somewhat effective, is time-consuming, taking at least two hours.

The preferred method is inactivating the plasma protease inhibitors relies on their sensitivity to acid-denaturation. Factors XI and XII and prekallikrein are relatively resistant to acid denaturation since their enzyme active sites are relatively inaccessible while the molecules are in the zymogen form. The plasma protease inhibitors, on the other hand, are substantially more sensitive to loss of activity by acid denaturation. Accordingly, the plasma protease inhibitors may be selectively inactivated by a brief, e.g. 15 minute, incubation of the subject plasma specimen with an equal volume of a dilute solution of strong acid, followed by stabilization with an appropriate buffer and neutralization with an equal volume of a dilute solution of strong base.

While the acid treatment may not be sufficient to remove all intrinsic protease inhibitor influence in the specimen attributable to alpha$_1$-antitrypsin, residual activity is effectively overcome by the subsequent steps of the assay. For example, the preferred prekallikrein/kallikrein inhibitor, soybean trypsin inhibitor, forms a weak complex with factor XI and protects it from residual alpha$_1$-antitrypsin activity not suppressed by the acid treatment. Furthermore, the plasma is diluted to a point where the residual alpha$_1$-antitrypsin will not inhibit the factor XIa. Thus, it is understood that substantial complete inactivation of plasma protease inhibitors in the specimen according to the method of the invention includes the case of substantial reduction of intrinsic plasma protease inhibitor activity by the acid pre-treatment as described above, with more complete reduction occurring upon the further steps of the assay as hereinafter provided.

The acid-treated plasma specimen may then be diluted with an appropriate buffer to a suitable dilution, e.g. 1:9 to 1:112 (equivalent to 1:36 to 1:450 dilution of plasma before the addition of other reagents) for conducting the assay.

Kallikrein accelerates activation of factor XII especially when it is surface-bound via HMWK. It may also hydrolyze the factor XIa substrate. Thus, prekallikrein activation should be substantially completely inhibited in the assay system to prevent generation of kallikrein. Any kallikrein already present should also be substantially completely inhibited. Any suitable agent or combination of agents, for inhibiting prekallikrein/kallikrein, which does not also substantially inactivate factor XIa under the conditions of the assay, may be employed. Such agents include plant inhibitors. Soybean trypsin inhibitor, available from Sigma Chemical Company, St. Louis, Missouri, is preferred since it not only selectively inhibits both prekallikrein activation and kallikrein activity, but also protects factor XIa from inactivation by any residual plasma protease inhibitor activity from the acid-treatment step.

Sufficient prekallikrein/kallikrein inhibitor should be added to the diluted plasma specimen under assay to substantially completely inhibit the prekallikrein/kallikrein present in the specimen in a reasonable length of time. For soybean trypsin inhibitor, this generally means adding an amount sufficient to establish a tenfold molar excess relative to the concentration of prekallikrein in the diluted specimen.

Upon inactivation of plasma protease inhibitors and inhibition of prekallikrein/kallikrein, exogenous factor XI may be introduced into the diluted specimen. When soybean trypsin inhibitor is employed as a prekallikrein/kallikrein inhibitor, it is advantageously pre-mixed with factor XI and thus added to the specimen simultaneously with factor XI to aid in preventing the latter from adhering to the assay vessel and to stabilize the factor XI/XIa.

Partially-purified human factor XI may be satisfactorily employed in the present assay. It may be isolated, for example, according to the method of Scott et al, *Blood* 63: 45–50 (1984), which is described in detail later.

Factor XI may also be isolated in substantially pure form by affinity chromatography using appropriate monoclonal or polyclonal antibodies. Mouse monoclonal antibodies to human factor XI have been reported by Sinha et al, *J. Biol. Chem.* 260: 10714–10719 (1985).

Factor XIIa is thereafter added to the system. Factor XIIa for use in the assay may be prepared by activating factor XII by incubation with purified human plasma kallikrein, followed by ion exchange chromotography to remove the kallikrein. Factor XII may be obtained for this purpose, for example, by the zinc chelate affinity chromatography method of Pixley et al, *Thromb. Res.* 41:89–98 (1986), which is described in detail later.

Factor XII is activated by incubation with purified human plasma kallikrein. The kallikrei is then removed by DEAE-Sephadex ion exchange chromatography according to Pixley et al, *J. Biol. Chem.* 260: 1723–1729 (1985) and a stock concentrated factor XIIa is prepared for use in the assay.

Care should be exercised in activating factor XII. The enzymatic form, factor XIIa, is unstable and spontaneously autoactivates to form factor XIIf, which will not activate factor XI.

The amounts of exogenous factor XI and XIIa introduced into the diluted specimen should be sufficient to establish a reaction mixture containing a molar excess of factor XI relative to HMWK. The amounts of factor XIIa and factor XI should further be selected such that for the particular temperature and reaction time employed for the activation of factor XI, not more than about 10%, preferably not more than about 5%, of the factor XI in the reaction mixture becomes converted to factor XIa. This will ensure that the concentration of functional HMWK in the reaction mixture is rate-limiting and directly proportional to the concentration of factor XI activated in the HMWK-dependent activation of factor XI by factor XIIa. Once the reaction proceeds beyond activation of about the initial 10% of available factor XI, the concentration of HMWK is no longer rate-limiting, and the relationship between the amount of functional HMWK in the system and the amount of factor XIa formed is no longer linear. Thus, the assay results to not reflect the concentration of functional HMWK in the specimen beyond activation of about the initial 10% of the available factor XI.

For economy and convenience, 30 minutes is the preferred reaction time for the room temperature (about 22° C.) activation of factor XI. Under these conditions, the amount of exogenous factor XIIa and factor XI added to form the reaction mixture should be such that the activation of factor XI proceeds in a reasonable amount of time. Beyond about 30 minutes reaction time at room temperature, under the conditions described, more than 10% of the factor XI in the reaction mixture becomes activated, and the concentration of functional HMWK is no longer linearly related to the concentration of factor XIa formed in the system.

The temperature, time of reaction, and concentration of factor XIIa and factor XI in the reaction mixture may be varied, provided that not more than about 10%, preferably not more than about 5%, of the factor XI in the specimen is activated to factor XIa.

The activation of factor XI proceeds upon the addition of a sufficient amount of an appropriate contact-activating surface to initiate the factor XIIa-dependent activation of factor XI. Negatively-charged surfaces are known to activate the zymogen factor XII, and subsequent activation of factor XI, in particular, requires an ample activating surface. Kaolin, diatomaceous earth (e.g. "CELITE," Johns-Manville Products Corp.) and micronized silica are surfaces upon which contact-activation of plasma occurs. Soluble contact activators such as ellagic acid and dextran sulfate are less suitable since they cause only minimal factor XI activation under the conditions of the assay and are more difficult to control. Kaolin (available, for example, as an acid washed powder from Fisher Scientific Chemical Co., King of Prussia, PA) is preferred.

Sufficient contact-activating surface should be added to the reaction mixture to provide a satisfactory reaction rate. If too little reagent is employed, the reaction will proceed at a slow rate. Too much reagent, on the other hand, may cause optical interference and impede spectrophotometric and microplate determination of factor XIa. The amount of surface will also limit the rate of factor XI activation since it will become saturated by the factor XI-HMWK complex.

While the order may be varied by which the prekallikrein/kallikrein inhibitor, factor XI, factor XIIa and acid-treated patient specimen are combined, it is preferred that the contact-activating surface be introduced into the system last. This is because factor XIIa is unstable, and will, in the presence of a contact-activating surface such as kaolin, spontaneously autoactivate to factor XIIf in the absence of substrate, causing a premature decrease in the amount of factor XIIa available to activate factor XI.

The reaction mixture containing the acid-treated specimen, prekallikrein/kallikrein inhibitor, exogenous factors XI and XIIa, and contact-activating surface, is then incubated for a sufficient period of time to allow conversion of not more than about 10%, and preferably not more than about 5%, of the available factor XI to the active enzyme factor XIa. The reaction may be promptly halted at this state by introducing an appropriate factor XIIa inactivating agent into the reaction mixture. The factor XIIa inactivating agent should be specific for factor XIIa and should not cause substantial inactivation of factor XIa under the conditions of the assay. Corn trypsin inhibitor, available from KabiVitrum, Mondal, Sweden, is preferred. Polyclonal or monoclonal antibodies specific to the active site of factor XIIa may be advantageously substituted for corn trypsin inhibitor. Sufficient factor XIIa inactivating agent should be added to the reaction mixture at this point to substantially completely inactivate factor XIIa in a reasonable time. Inactivation of factor XIIa in this manner leaves factor XIa as the only enzyme remaining in the assay system that can effectively hydrolyze the substrate.

Once factor XIIa is substantially completely inactivated in the reaction mixture, the amount of factor XIa formed, and thus the amount of functional HMWK contained in the specimen, may be determined by an appropriate functional assay for factor XIa using an appropriate natural or synthetic factor XIa substrate.

According to one embodiment, a chromogenic substrate for factor XIa is incubated with the assay reaction mixture. The substrate should, under the conditions of the assay, be capable of hydrolysis by factor XIa to yield a hydrolysis product whose appearance may be monitored spectrophotometrically or by a microplate reader. Such substrates include, for example, L-pyroglutamyl-L-prolyl-L-arginine-p-nitroanilide and H-D-leucylthreonyl-arginine-p-nitroanilide, available from KabiVitrum in hydrochloride form as "S-2366" and "S-2511", respectively. The enzymatic activity of factor XIa catalyzes the hydrolysis of the peptide-p-nitroanilide bond, releasing the chromophore p-nitroaniline.

The appearance of p-nitroaniline may be measured spectrophotometrically after a fixed hydrolysis time, at 405 nm. The change in absorbance is proportional to the enzyme activity.

H-D-prolyl-prolyl-arginine-p-nitroanilide, available from American Diagnostica Inc., Greenwich, CN as "SPECTROZYME PCa" and D-lysyl(epsilon-benzoyloxycarbonyl)-L-prolyl-L-arginine-p-nitroanilide, which will become available from Diagnostica Stago, Asnifres, France in 1987 as "STACHROM" Protein C, are two further chromogenic substrates which may be useful in the assay of the present invention.

Tert-butoxycarbonyl-phenylalanyl-seryl-arginine-7-amino-4-methylcoumarin and tert-butoxycarbonyl-leucylthreonyl-arginine-7-amino-4-methylcoumarin have been demonstrated by Iwanaga et al *Adv. Exp. Med. Biol.* 120: 147-163 (1974) to be fluorogenic substrates for factor XIa. It is believed that these substrates are useful in the present assay. They may be synthesized by standard chemicl procedures, using L-amino acids.

While only chromogenic and fluorogenic substrates have been identified, synthetic peptides mimicking the active site of natural factor XIa substrates may be labelled at the C-terminal amino acid with luminogenic, radioactive or other suitable markers and used as substrates for factor XIa in the assay method.

Suitably labelled natural factor XIa substrates, e.g. radiolabelled factor IX, may likewise be employed. Factor IX may be tritium-labelled for this purpose according to the method of Walsh et al, *J. Clin. Invest.* 73: 1392-1399 (1984). Walsh et al observed a linear relationship between the concentration of factor XIa and the initial rate of release of a trichloracetic acid-soluble tritium-labelled activation peptide from factor IX.

S-2366 is the preferred substrate. It displays a $K_{cat}$ to $K_m$ ratio of $5.5 \times 10^6 M^{-1} sec^{-1}$, making it very suitable for human factor XIa.

The assay may be terminated following hydrolysis of the substrate by the available factor XIa by adding a solution of 50% acetic acid or 1M sodium citrate. This has the effect of denaturing active proteins possibly remaining in the reaction mixture and the low pH prevents hydrolysis of the substrate. Samples treated in this manner are stable overnight, and may be read the following day.

Dilution of the acid-treated plasma specimen and all reagents used in the procedure are preferably carried out in a buffer of 20 mM Tris-Cl pH 7.4, containing 0.15m NaCl, 1 mM ethylenediaminetetraacetate (EDTA), and 0.1% polyethylene glycol (PEG), hereinafter referred to as "Working Buffer". The ionic strength and pH of the Working Buffer approximate that of human plasma. Polyethylene glycol has the highly advantageous property of minimizing sticking of the plasma factors utilized in the assay to the walls of the assay vessel.

The proteins used in the assay may become denatured at the dilutions employed. Bovine serum albumin may be utilized to stabilize the proteins. A small amount, i.e., 0.2 mg/ml of bovine serum albumin is thus preferably added to each working protein solution used in the assay.

The amount of factor XIa substrate introduced into the reaction mixture, and the temperature and reaction time of the factor XIa-catalyzed substrate hydrolysis reaction are selected such that the concentration of factor XIa hydrolyzes not more than about 10%, and preferably not more than about 5%, of the substrate.

Hydrolysis beyond about the initial 10% of available substrate will cause a slowing of the hydrolysis reaction and deviation from linearity, such that absorbance is no longer directly proportional to the concentration of hydrolyzed substrate. It is only during the initial stage of the hydrolysis reaction that the reaction rate is directly proportional to the concentration of factor XIa, and therefore to the concentration of functional HMWK. Furthermore, the maximum optical density generated by factor XIa and the chromogenic substrate should not exceed 0.9 optical density units to ensure optical linearity according to Beer's Law.

Since factor XIIa and factor XI are supplied in the assay in excess of the amount of HMWK present in the specimen, and kallikrein is inhibited, the concentration of HMWK becomes rate-limiting. The assay method specifically measures functional HMWK and does not result in a spuriously low value due to a deficiency of one or more of the other contact factors. Inactivation of plasma protease inhibitors by treating the plasma specimen prior to assay assures that factor XIa, once formed, and exogenous factor XIIa, remain functional.

Since the assay is performed under conditions where a linear relationship exists between HMWK concentration and the formation of factor XIa, the amount of factor XIa produced is directly proportional to the amount of HMWK in the specimen. Since factor XIa is the only enzyme active in the reaction mixture following inactivation of factor XIIa and kallikrein, the amount of factor XIa substrate hydrolyzed directly reflects the amount of factor XIa formed, and in turn reflects the concentration of functional HMWK in the reaction mixture.

Partially-purified factor XI may be prepared for use in the assay by the following method of Scott et al, *Blood* 63:45-50 (1984), it being expressly understood however that other suitable methods for partially purifying factor XI are known to those skilled in the art.

PREPARATION OF PARTIALLY-PURIFIED FACTOR XI

Nine hundred milliliters of fresh-frozen plasma containing 50 micrograms/ml hexadimethrine bromide, 1 mM EDTA, and 0.02% sodium azide, is mixed with a batch of QAE-Sephadex and then filtered. The filtrate is sequentially mixed with 2 additional batches of QAE-Sephadex (900-ml slurry in 20 mM Tris-Cl, pH 8.1). The material which does not adsorb is mixed with 1,000 ml SP-Sephadex equilibrated with 20 mM Tris-Cl, pH 8.1 (conductivity adjusted to less than 2 mmho), mixed for 30 min, and filtered. The resin containing the adsorbed protein is poured into a column and eluted by a linear gradient between 0 and 0.13M NaCl. The fractions containing factor XI coagulant activity are pooled and concentrated. The resulting preparation of partially-purified factor XI, which may contain trace amounts of prekallikrein and variable amounts of gamma globulin, may be employed in the assay. The trace amounts of prekallikrein may be optionally removed from the fractions containing factor XI coagulant activity by concentration and dialysis in an Amicon concentrator (PM-30 membrane) versus 0.1M sodium acetate, pH 5.3, followed by SP-Sephadex chromotrography. Factor XI is eluted by a linear gradient from 0 to 0.35M NaCl. The fractions containing factor XI coagulant activity, which contain IgG as the only contaminant, are pooled and concentrated.

Factor XII for conversion to factor XIIa and use in the assay may be prepared by following the method of Pixley et al, *Thromb. Res.* 41:89-98 (1986), it being expressly understood that other suitable methods for isolating factor XII are known to those skilled in the art.

PREPARATION OF FACTOR XII

Plastic containers and columns are used throughout the purification procedure. All dialysis tubing and plastic containers are prerinsed with 2 mg/ml of hexadimethrine bromide in $H_2O$, then rinsed with $H_2O$. All steps are carried out at room temperature except where indicated. Concentration of factor XII is performed by negative pressure dialysis at 4° C.

Fresh frozen plasma (4005 ml) containing 4% sodium citrate as anticoagulant is quickly thawed in a polypropylene container at 37° C. containing soybean trypsin inhibitor (SBTI) (0.1 mg/ml) and hexadimethrine bromide (0.36 mg/ml).

Ammonium Sulfate Precipitation, 25-50%

Crystalline ammonium sulfate (144 g/L plasma) is slowly dissolved in the plasma and stirred for 30 minutes. The solution is centrifuged at 13,680×g, for 30 minutes. Ammonium sulfate (158 g/L) is slowly dissolved in the decanted supernatant at room temperature and stirred for 60 minutes. The mixture is centrifuged at 13,680×g for 60 minutes. The precipitate is dissolved in minimal amounts (1 liter) of 0.025M $Na_2HPO_4$, 0.8M NaCl, 0.2 mg/ml SBTI, 0.36 mg/ml hexadimethrine bromide, 0.02% $NaN_3$, pH 6.5, and dialyzed overnight against two changes of 20 liters of the same buffer without SBTI at 4° C.

Zinc Chelate Chromatography #1

The solution is centrifuged for 10 minutes at 4000×g to remove precipitate formed during dialysis. Three hundred ml of equilibrated Zinc Chelate Sepharose (Pixley et al., *J. Biol. Chem.* 260: 1723-1729 (1985)) is placed in a plastic Buchner funnel under low vacuum. The solution is slowly allowed to flow through the resin and collected. The resin is washed with equilibrating buffer and collected in 500 ml fractions until the absorbance readings at 280 nm is below 0.1 (approximately 11 liters). The resin is then washed with 2 to 3 liters cacodylate buffer (0.02M sodium cocodylate, 0.15M NaCl, 0.1 mg/ml SBTI, 0.03 mg/ml hexadimethrine bromide, 0.02% $NaN_3$, pH 5.5) until the absorbance readings of the fractions are below 0.1. Factor XII fractions are eluted with 10 liters of acetate buffer (0.1M sodium acetate, 0.8M NaCl, 0.1 mg/ml SBTI, 0.03 mg/ml hexadimethrine bromide, 0.02% $NaN_3$, pH 4.5) and assayed for factor XII coagulant activity.

The factor XII fractions are pooled and dialyzed overnight against two changes of 20 liters of Phosphateacetate buffer (0.025M $Na_2HPO_4$, 0.005M sodium acetate, 0.8M NaCl, 0.001 mg/ml hexadimethrine bromide, 0.02% $NaN_3$, pH 6.5) at 4° C.

Zinc Chelate Chromatography #2

The dialized factor XII fractions are applied to a column (2.5×25 cm) containing 120 ml of Phosphate-acetate buffer equilibrated Zinc Chelate Sepharose and washed overnight with 2 liters of the same buffer at a flow rate of 100 ml/hr. A pH gradient of 250 ml each of the Phosphate-acetate buffer at pH 6.5 and 4.0, followed by a 100 ml wash of pH 4.0 buffer is applied to the column and 5 ml fractions are collected. Five hundred microliter aliquots are placed in polypropylene Eppendorf tubes for analysis and the fractions and aliquots are frozen at −70° C.

The gradient aliquots are analyzed for protein, factor XII coagulant activity, Kabi S-2302 (chromogenic substrate for plasma kallikrein and factor XIIa, KabiVitrum, Mondal, Sweden) amidolytic activity, and then subjected to SDS-PAGE. The fractions determined to contain factor XII are pooled and concentrated in portions by negative pressure dialysis against Phosphate-acetate buffer, pH 6.5

Gel Filtration

Aliquots containing 50-100 units of factor XII coagulant activity are applied to a 1.5×88 cm column of Biogel A 0.5 equilibrated with Phosphate-acetate buffer at a flow rate of 1 ml/min. Two ml fractions are collected and analyzed for protein, coagulant activity, and S-2303 amidolytic activity, and subjected to SDS-PAGE. The 2 ml fractions are frozen. The fractions determined to contain purified factor XII are thawed and concentrated by negative pressure dialysis against Phosphate-acetate buffer. When the volume is 5-7 ml, the buffer is changed to 0.05M Tris, 0.05M NaCl, 0.1% PEG 8000, pH 8.0 for activation to factor XIIa.

Factor XII isolated according to this method is homogeneous at 78 kDa according to SDS-PAGE, and has a specific activity of 80 U/mg, one unit of factor XII being defined as the amount present in 1 ml of a pooled normal plasma, equivalent to a concentration of 0.37 micromolar.

The following non-limiting example is intended to illustrate the assay of the present invention using a microplate reader.

EXAMPLE 1

Removal of Plasma Protease Inhibitor Influence

Human plasma is treated as follows to inactive plasma protease inhibitors. 50 microliters of human plasma is mixed with 50 microliters of 1/6N hydrochloric acid at room temperature and allowed to stand for 15 minutes. Fifty microliters of a buffer comprising 0.1M sodium phosphate, pH 7.6, containing 0.15M sodium chloride, 1 mM EDTA and 0.4% PEG, is then added to the plasma, followed by 50 microliters of 1/6N sodium hydroxide and mixing. Plasma treated accordingly is hereinafter referred to as "acid-treated plasma".

Preparation of Reference Standard

Fifty microliters of pooled acid-treated normal plasma (from at least 20 individuals) is added to 400 microliters of Working Buffer. The concentration of HMWK in the thus-treated plasma is arbitrarily assigned a value of 125% as a reference standard. The 125% reference plasma is then serially diluted with Working Buffer as in Table I to generate a standard curve for relative functional HMWK concentration:

TABLE I

| Dilution of Reference Standard | | |
|---|---|---|
| 125% Reference Plasma | Buffer Added | % HMWK |
| 100 microliters | 25 microliters | 100 |
| 75 microliters | 50 microliters | 75 |
| 50 microliters | 75 microliters | 50 |
| 25 microliters | 100 microliters | 25 |
| 10 microliters | 115 microliters | 10 |
| 0 microliters | 125 microliters | 0 |

Assay Procedure

Reagents A through F are prepared as in Table II, reagents A through D being prepared in Working Buffer:

TABLE II

| Reagents |
|---|
| A. 0.5 U/ml Factor XI containing 5 micromolar soybean trypsin inhibitor and 0.2 mg/ml bovine serum albumin |
| B. 0.10 U/ml Factor XIIa containing 0.2 mg/ml bovine serum albumin |
| C. 0.625 mg/ml kaolin |
| D. 0.1 mg/ml corn trypsin inhibitor |
| E. 4.6 mM S-2366 |
| F. 50% acetic acid |

A standard curve for functional HMWK using the reference standards prepared from pooled normal plasma may be generated as follows, all steps being conducted at room temperature. Twenty-five microliters of each reference solution from Table I are placed in separate wells of a 96 well tissue culture-treated microplate (e.g. Falcon Plastics, Mt. Laurel, New Jersey, #3072 or #3075). Thirty-five microliters of Reagent A is added to each well, followed by 25 microliters of Reagent B, and 15 microliters of Reagent C. The mixture is then incubated for thirty minutes. The concentration of factor XI and XIIa in the mixture are 8.75 nM and 9.75 nM respectively, while the concentration of kaolin is 93 micrograms per ml. Ten microliters of Reagent D is added to the mixture to establish a final concentration of corn trypsin inhibitor of 7 micromolar. The mixture is allowed to incubate for an additional 10-15 minutes. Fifty microliters of Reagent E is added to establish a final concentration of S-2366 of 1.375 mM. The mixture is incubated for 45-90 minutes further. Finally, 100 microliters of Reagent F is added to each well. The microplate is read at 405 nm in a suitable microplate-reader apparatus, such as Model 2550 EIA Microplate Reader, Bio-Rad, Inc., Richmond, CA.

The absorbence at 405 nm is plotted versus the assigned HMWK percentages of Table I to generate a standard curve of functional HMWK concentration versus absorbance. The standard curve shown in the Figure was generated from a pool of 20 normal (acid-treated) plasmas serially diluted with buffer (x), or with HMWK-deficient plasma (o). The Figure indicates that the same curve was obtained substituting HMWK-deficient plasma for buffer as the diluent, thereby establishing the specificity of the assay for HMWK.

Plasma specimens of unknown functional HMWK concentration are assayed simultaneously with the reference samples which are used to generate the standard curve. The specimens are treated to remove plasma protease inhibitor influence in the same manner as the reference standard. Forty microliters of the resulting acid-treaded plasma specimen are added to 410 microliters of Working Buffer. The plasma in the specimen is now at the identical dilution as the "100% HMWK" reference standard of Table I. The same procedure described above, utilizing Reagents A through F, is carried out on the specimen and the absorbence at 405 nm is compared to the standard curve. The amount of functional HMWK in the specimen is thus expressed as a percentage of normal plasma. The data may be conveniently expressed in "units per ml", one unit per ml being defined as 100% of the amount of functional HMWK in one ml of normal, pooled reference plasma.

If a spectrophotometer is used in place of a microplate reader, all incubations should be done in plastic disposable test tubes and the assay should be scaled up two- to four-fold, depending on the size of the spectrophotometer cuvette.

The following non-limiting example is intended to illustrate the assay of the present invention using a spectrophotometer.

EXAMPLE 2

One hundred microliters of a reference solution from Table I, or 100 microliters of acid-treated plasma specimen diluted with Working Buffer as in Example 1, are added to 140 microliters of Reagent A in a plastic test tube followed by 100 microliters of Reagent B and 60 microliters of Reagent C. The tube is covered and the mixture is incubated for 30 minutes at room temperature, or for 10 minutes at 37° C. Forty microliters of Reagent D is added and the mixture is incubated for 10-15 minutes at room temperature or 37° C. Two hundred microliters of Reagent E is added and the mixture is incubated 45-90 minutes at room temperature or 15-30 minutes at 37° C. Finally, 400 microliters of Reagent F is added to the test tube. Each sample is read at 405 nm in a 1 ml capacity cuvette. For microcuvettes, the same volumes provided in Example 1 should be used.

Incubating 8.75 nM factor XI with 9.25 nM factor XIIa, the same concentration employed in Example 1, revealed that factor XI may activate in the absence of HMWK. This HMWK-independent activation of factor XI is directly proportional to the concentration of factor XIIa present. Since this baseline absorbance value attributable to HMWK-independent factor XI activation is subtracted from all HMWK determinations (0%) the only factor XI activation measured in the assay is the HMWK-dependent activation caused by factor XIIa.

Under the conditions of the assay provided for in the examples, and choosing the amounts of reagents stated therein, the activation of factor XI appears to plateau between 3.5 and 5.5 nM factor XIIa, independent of the concentration of HMWK in the incubation mixture. Varying the incubation time up to 30 minutes maintains the linear dependence between absorbance and functional HMWK concentration. At 45 minutes, deviation from linearity is observed. Therefore, 30 minutes appears to be an appropriate incubation time to ensure linearity. If, under the conditions of the assay provided for in the above examples, conditions of the assay provided for in the above examples, and using the amounts reagents stated therein, an absorbance of 0.75 is attained after subtracting the buffer-S-2366 blank, 10% of the available factor XI in the reactive mixture will be consumed. Under the conditions of the assay, not more than 10% of the chromogenic substrate is consumed.

Plasma from each of twenty-one normal donors was assayed for functional HMWK by the coagulant-activity method of Scott et al. *J. Clin. Invest.* 73: 954-962 (1984), and according to the chromogenic assay of the present invention using an microplate reader. The mean value HMWK activity for the 21 donors according to the coagulant assay was 0.99 U/ml. HMWK activity for the same donors measured by chromogenic assay ranged from 0.68 to 1.28 U/ml, with a mean of 0.98 U/ml.

When compared with the prior art HMWK coagulant assay, the chromogenic assay has a coefficient of correlation equal to 0.95.

The assay is specific for HMWK, and can be performed on as many as forty samples in duplicate in less than two hours in a microplate system. The assay is highly reproducible, having a coefficient of variation of less than 2%. It may be performed in a clinical laboratory or intensive care unit setting to monitor the progress of pathological conditions in which contact activation occurs, signalled by changes in HMWK plasma levels. Moreover, the assay may find utility in the dental office in assessing the severity of periodontal disease, which results in local stimulation of the contact activation system.

The system is advantageously adapted to kit form. A kit may, for example, contain the concentrated reagents of Table III which may be reconstituted with distilled water or Working Buffer was provided in Table III.

TABLE III

| | |
|---|---|
| Vial #1 | factor XI, 3.5 U; bovine serum albumin, 1.4 mg; soybean trypsin inhibitor, 0.735 mg (lyophilized from Working Buffer); reconstitute with distilled water to 7 ml |
| Vial #2 | factor XIIa, 0.50 U; bovine serum albumin, 1 mg; PEG, 5 mg (lyophilized from Working Buffer); reconstitute with distilled water to 5 ml |
| Vial #3 | kaolin, 2.5 mg; PEG 4 mg; reconstitute to 4 ml with Working Buffer |
| Vial #4 | corn trypsin inhibitor, 0.2 mg (lyophilized from Working Buffer); reconstitute to 2 ml with distilled water |
| Vial #5 | S-2366, 25 mg; reconstitute to 10 ml with distilled water |
| Vial #6 | 3 ml of stock buffer containing 200 mM Tris-Cl (pH 7.4), 1.5 M NaCl, 1% PEG, 10 mM EDTA; dilute 1:10 with distilled water to form the Working Buffer |

The present invention may be embodied in other specific forms without departing from the spirit or essential attributes thereof and, accordingly, reference should be made to the appended claims, rather than to the foregoing specification, as indicating the scope of the invention.

What is claimed is:

1. An assay method for functional high molecular weight kininogen (HMWK) in plasma comprising:
   (a) substantially completely inactivating plasma protease inhibitors in a plasma specimen;
   (b) substantially completely inhibiting prekallikrein activation and kallikrein activity in the specimen;
   (c) forming a reaction mixture comprising said specimen, a contact-activating surface and selected amounts of factor XIIa and factor XI to initiate HMWK-dependent activation of factor XI in the reaction mixture, the amounts of factor XIIa and factor XI being selected such that at a predetermined temperature and predetermined reaction time the concentration of functional HMWK in the reaction mixture is rate-limiting in the HMWK-dependent activation of factor XI and directly proportional to the concentration of factor XIa generated in the reaction mixture;
   (d) substantially completely inactivating factor XIIa in the reaction mixture at the predetermined reaction time; and
   (e) assaying the amount of factor XIa formed in the reaction mixture by measuring the hydrolysis of a substrate for factor XIa, said amount of factor XIa being directly proportional to the amount of functional HMWK in the plasma specimen.

2. A method according to claim 1 wherein not more than about 10% of the factor XI in the reaction mixture is converted to factor XIa.

3. A method according to claim 2 wherein not more than about 5% of the factor XI in the reaction mixture is converted to factor XIa.

4. A method according to claim 1 wherein the assay of factor XIa in step (e) is by proteolysis of a natural factor XIa substrate.

5. A method according to claim 1 wherein the assay of factor XIa in step (e) is by hydrolysis of a radiolabelled substrate for factor XIa.

6. A method according to claim 1 wherein the assay of factor XIa in step (e) comprises hydrolysis of a chromogenic substrate of factor XIa.

7. A method according to claim 1 wherein the assay of factor XIa in step (e) comprises hydrolysis of a fluorogenic substrate of factor XIa.

8. A method according to claim 1 wherein not more than about 10% of a factor XIa substrate is hydrolyzed in the assay of factor XIa in step (e).

9. A method according to claim 6 wherein the chromogenic substrate is selected from the group consisting of L-pyroglutamyl-L-prolyl-L-arginine-p-nitroanilide, H-D-leucylthreonyl-arginine p-nitroanilide, H-D-prolyl-prolyl-arginine-p-nitroanilide and D-lysl(epsilon-benzoyloxycarbonyl)-L-prolyl-L-arginine-p-nitroanilide.

10. A method according to claim 7 wherein the fluorogenic substrate is selected from the group consisting of tert-butoxycarbonyl-phenylalanyl-seryl-arginine-7-amino-4-methylcoumarin and tert-butoxycarbonyl-leucyl-threonylarginine-7-amino-4-methylcoumarin.

11. A method according to claim 9 wherein the chromogenic substrate is L-pyroglutamyl-L-prolyl-L-arginine-p-nitroanilide.

12. A method according to claim 1 wherein prekallikrein activation and kallikrein activity are inhibited in step (b) by soybean trypsin inhibitor.

13. A method according to claim 12 wherein soybean trypsin inhibitor and factor XI are premixed and added to the specimen simultaneously in step (b).

14. A method according to claim 1 wherein inactivation of factor XIIa in step (d) is by corn trypsin inhibitor.

15. A method according to claim 1 wherein inactivation of plasma protease inhibitors in step (a) comprises treatment of the specimen with acid.

16. A method according to claim 1 wherein the contact-activating reagent is added to the reaction mixture after factor XI and factor XIIa are added to the reaction mixture.

17. A chromogenic assay for functional high molecular weight kininogen (HMWK) in a plasma specimen comprising:
 (a) substantially completely inactivating plasma protease inhibitors in a plasma specimen;
 (b) adding soybean trypsin inhibitor, factor XIIa, factor XI and a contact-activating surface to the specimen to form a reaction mixture for the HMWK-dependent activation of factor XI, the amount of soybean trypsin inhibitor added to the specimen being sufficient to establish a molar excess of soybean trypsin inhibitor to prekallikrein in the reaction mixture, the amount of factor XIIa added to the specimen being sufficient to establish a molar excess of factor XIIa to HMWK in the reaction mixture;
 (c) incubating said reaction mixture for a time sufficient to activate not more than about 10% of the factor XI in the reaction mixture to factor XIa;
 (d) preventing further activation of factor XI by adding sufficient corn trypsin inhibitor to the reaction mixture to establish a molar excess of corn trypsin inhibitor to factor XIIa in the reaction mixture; and
 (e) assaying the amount of factor XIa formed in the reaction mixture by measuring the hydrolysis of a chromogenic substrate for factor XIa, said amount of factor XIa being directly proportional to the amount of functional HMWK in the plasma specimen.

18. An assay according to claim 17 wherein not more than about 5% of the factor XI in the mixture is converted to factor XIa.

19. An assay according to claim 17 wherein the molar ratio of soybean trypsin inhibitor to prekallikrein is at least about 10:1 and the molar ratio of corn trypsin inhibitor to factor XIIa is at least about 5:1.

20. An assay according to claim 17 wherein the contact-activating reagent is kaolin.

21. An assay according to claim 17 wherein the chromogenic substrate is L-pyroglutamyl-L-prolyl-L-arginine-p-nitroanilide.

* * * * *

UNITED STATES PATENT AND TRADEMARK OFFICE
CERTIFICATE OF CORRECTION

PATENT NO. : 4,882,272

DATED : November 21, 1989

INVENTOR(S) : Cheryl F. Scott et al.

It is certified that error appears in the above-identified patent and that said Letters Patent is hereby corrected as shown below:

Column 4, line 57: Change "is" to --of--; column 6, line 12: change "kallikrei" to --kallikrein--; column 6, line 15: insert --of-- after "stock"; column 6, line 40: change "to" to --do--; column 7, line 40: change "Mondal" to --Mölndal--; column 13, lines 51 and 52: delete "conditions of the assay provided for in the above examples,"; column 13, line 52: insert --of-- after "amounts"; column 13, line 64: insert --of-- after "value"; claim 9, line 4: insert a dash (-) between "arginine" and "p"; claim 10, line 4: insert a dash (-) between "threonyl" and "arginine"; claim 19, last line: change "5:1" to --50:1--.

Signed and Sealed this

Nineteenth Day of February, 1991

Attest:

HARRY F. MANBECK, JR.

*Attesting Officer*    *Commissioner of Patents and Trademarks*